US011864825B2

(12) United States Patent
Highsmith

(10) Patent No.: US 11,864,825 B2
(45) Date of Patent: Jan. 9, 2024

(54) ABLATION CATHETER WITH SELECTIVE RADIAL ENERGY DELIVERY

(71) Applicant: Biosense Webster (Israel) Ltd., Yokneam (IL)

(72) Inventor: Debby Highsmith, Laguna Niguel, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 644 days.

(21) Appl. No.: 15/969,579

(22) Filed: May 2, 2018

(65) Prior Publication Data

US 2019/0336205 A1     Nov. 7, 2019

(51) Int. Cl.
*A61B 18/14*     (2006.01)
*A61B 18/12*     (2006.01)
*A61B 18/00*     (2006.01)

(52) U.S. Cl.
CPC .......... *A61B 18/1492* (2013.01); *A61B 18/12* (2013.01); *A61B 18/14* (2013.01); *A61B 2018/00011* (2013.01); *A61B 2018/0016* (2013.01); *A61B 2018/00029* (2013.01); *A61B 2018/00351* (2013.01); *A61B 2018/00577* (2013.01); *A61B 2018/00636* (2013.01); *A61B 2018/00702* (2013.01);
(Continued)

(58) Field of Classification Search
CPC ........ A61B 18/1492; A61B 2018/0016; A61B 2018/1497; A61B 2018/1467; A61B 18/12; A61B 18/14; A61B 2018/00636;
A61B 2018/00029; A61B 2018/00875; A61B 2018/124; A61B 2018/00839; A61B 2018/00011; A61B 2018/00351; A61B 2018/00577; A61B 2018/00702; A61B 2018/00791; A61B 2218/002
See application file for complete search history.

(56) References Cited

U.S. PATENT DOCUMENTS 5,391,199 A     2/1995  Ben-Haim
5,462,545 A *  10/1995  Wang ................. A61B 18/1492
                                                                    606/41
(Continued)

FOREIGN PATENT DOCUMENTS

JP     2014113493 B2    6/2014
JP     2017504401 A1    2/2017
(Continued)

OTHER PUBLICATIONS

Extended European Search Report in European Patent Application No. 19172110.9, dated Sep. 30, 2019.
(Continued)

*Primary Examiner* — Sean W Collins
(74) *Attorney, Agent, or Firm* — Dergosits & Noah LLP; Todd A. Noah

(57) ABSTRACT

An electrode assembly for use with an electrophysiological catheter has a plurality of independently controlled ablation electrodes distributed radially around the electrode assembly. Two ablation electrodes may be positioned in opposition to each other. The electrode assembly may also have microelectrodes for sensing tissue and/or temperature. Methods for using a catheter equipped with such an electrode assembly may include preferentially emitting energy in a radial direction.

8 Claims, 5 Drawing Sheets

(52) U.S. Cl.
CPC ............... *A61B 2018/00791* (2013.01); *A61B 2018/00839* (2013.01); *A61B 2018/00875* (2013.01); *A61B 2018/124* (2013.01); *A61B 2018/1467* (2013.01); *A61B 2018/1497* (2013.01); *A61B 2218/002* (2013.01)

(56) References Cited

U.S. PATENT DOCUMENTS

| | | | |
|---|---|---|---|
| 6,064,905 A | 5/2000 | Webster, Jr. et al. | |
| 6,239,724 B1 | 5/2001 | Doron et al. | |
| 6,241,724 B1 * | 6/2001 | Fleischman | A61B 18/1492 600/374 |
| 6,332,089 B1 | 12/2001 | Murphy | |
| 6,468,262 B1 | 10/2002 | Murphy | |
| 6,484,118 B1 | 11/2002 | Govari | |
| 6,500,167 B1 | 12/2002 | Webster, Jr. | |
| 6,522,933 B2 | 2/2003 | Nguyen | |
| 6,618,612 B1 | 9/2003 | Acker et al. | |
| 6,690,963 B2 | 10/2004 | Ben-Haim et al. | |
| 7,729,742 B2 | 6/2010 | Govari | |
| 8,147,486 B2 | 4/2012 | Honour et al. | |
| 8,437,832 B2 | 5/2013 | Govari et al. | |
| 8,496,653 B2 | 7/2013 | Steinke | |
| 8,617,087 B2 | 12/2013 | Schultz | |
| 8,954,161 B2 | 2/2015 | McCarthy et al. | |
| 9,023,036 B2 | 5/2015 | Govari et al. | |
| 9,037,259 B2 | 5/2015 | Mathur | |
| 9,636,164 B2 | 5/2017 | Panescu et al. | |
| 9,675,411 B2 | 6/2017 | Govari et al. | |
| 9,743,981 B2 | 8/2017 | Huszar et al. | |
| 10,653,480 B2 | 5/2020 | Beeckler et al. | |
| 11,202,671 B2 | 12/2021 | Hanson et al. | |
| 2004/0068178 A1 | 4/2004 | Govari | |
| 2007/0219551 A1 | 9/2007 | Honour et al. | |
| 2011/0130648 A1 | 6/2011 | Beeckler et al. | |
| 2014/0163546 A1 * | 6/2014 | Govari | A61B 18/1492 606/34 |
| 2014/0275921 A1 | 9/2014 | Harlev et al. | |
| 2015/0119882 A1 * | 4/2015 | Cao | A61B 18/1492 606/41 |
| 2015/0272667 A1 * | 10/2015 | Govari | A61B 18/1206 606/41 |
| 2015/0327921 A1 * | 11/2015 | Govari | A61B 5/0538 606/41 |
| 2015/0366508 A1 | 12/2015 | Chou et al. | |
| 2016/0073960 A1 | 3/2016 | Jung et al. | |
| 2016/0228061 A1 * | 8/2016 | Källbäck | A61B 5/0215 |
| 2017/0042615 A1 | 2/2017 | Salahieh et al. | |
| 2017/0156791 A1 | 6/2017 | Govari | |
| 2017/0312022 A1 | 11/2017 | Beeckler et al. | |
| 2017/0333125 A1 | 11/2017 | Lepak et al. | |

FOREIGN PATENT DOCUMENTS

| | | |
|---|---|---|
| JP | 2017202305 A | 11/2017 |
| WO | WO 96/05768 | 2/1996 |

OTHER PUBLICATIONS

Notification of Reasons for Refusal from correspondending Japanese Patent Application No. 2019-085218 dated Apr. 17, 2023.
Communication from corresponding European Patent Application No. 19172110.9 dated Sep. 23, 2020.

* cited by examiner

ABLATION CATHETER WITH SELECTIVE RADIAL ENERGY DELIVERY

FIELD OF THE PRESENT DISCLOSURE

This invention relates to electrode assemblies for use with electrophysiologic (EP) catheters and related devices for mapping and/or ablation of locations within a patient, such as the heart, in particular, to an ablation catheter having selective radial control over delivery of radio frequency (RF) energy.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Procedures for treating arrhythmia include surgically disrupting the origin of the signals causing the arrhythmia, as well as disrupting the conducting pathway for such signals. More recently, it has been found that by mapping the electrical properties of the heart and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions. The resulting lesion(s) may isolate irregular electrical signals originating in the one area from spreading and disrupting the patient's heart beat.

In such procedures, a reference electrode is typically provided and may be attached to the skin of the patient or by means of a second catheter. Radio frequency (RF) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the target tissue resulting in formation of a lesion which is electrically non-conductive.

As an example of such applications, recent techniques have employed ablation to treat ventricular tachycardia. The technique involves introducing a catheter into the pericardial space, such as by using a subxiphoid pericardial puncture technique. The parietal pericardium is the outer protective layer or sac that encloses the heart which comprises three layers: epicardium, myocardium and endocardium. A pericardial cavity or space separates the parietal pericardium and the epicardium. A small amount of fluid is secreted by tissues of the parietal pericardium to lubricate surfaces so that heart can move freely inside the parietal pericardium. Clearly, adhesion between the parietal pericardium and the epicardium caused by misdirected ablation energy may interfere with muscular contractions of the heart.

Another potential complication in accessing the epicardium is posed by the phrenic nerve. The phrenic nerve is made up mostly of motor nerve fibers for producing contractions of the diaphragm. In addition, it provides sensory innervation for many components of the mediastinum and pleura, as well as the upper abdomen, especially the liver, and the gall bladder. The right phrenic nerve passes over the right atrium and the left phrenic nerve passes over the left ventricle and pierces the diaphragm separately. Both these nerves supply motor fibers to the diaphragm and sensory fibers to the fibrous pericardium, mediastinal pleura and diaphragmatic peritoneum. Any damage to the phrenic nerve, particularly for senior patients, can cause serious breathing difficulties, especially if the damage is permanent. The lung itself is another organ that is susceptible to damage when ablating the epicardium, although the tissue of the lung can more readily repair itself if burned.

Conventional ablation catheters have primarily been designed for endocardial uses and do not exhibit optimal delivery of energy for epicardial applications. While such catheters are particularly useful for mapping and ablating in cavities and other tubular regions of or near the heart, the omnidirectional delivery of energy in the epicardium may significantly increase the risk of harmful and unwanted ablation, such as of the parietal pericardium, the phrenic nerve, the lungs and/or other surrounding structures. For example, ring electrodes positioned along a distal portion of the catheter emit energy from their entire circumference, with only a portion being directed at the intended treatment area. Likewise, a distal dome electrode primarily emits energy along the longitudinal axis of the catheter rather than being directed towards the epicardial tissue surface.

Accordingly, it would be desirable for a catheter to be adapted for the epicardium such that the ablation energy is directed in a radially selective manner to reduce exposure of unwanted regions as well as optimize the ablation by directing energy only to desired locations. Likewise, it would be desirable sense tissue contact or proximity so as to preferentially direct energy towards the intended treatment area. As will be described in the following materials, this disclosure satisfies these and other needs.

SUMMARY

The present disclosure is directed to an electrode assembly configured to be disposed over a distal portion of a catheter body, wherein the electrode assembly has a flexible substrate and a plurality of independently controlled ablation electrodes distributed radially around the electrode assembly.

In one aspect, two ablation electrodes may be positioned in opposition to each other. Alternatively, the electrode assembly may have more than two ablation electrodes.

In one aspect, the electrode assembly may be configured as a cylinder. The ablation electrodes may be applied to an outer surface of the substrate.

In one aspect, at least one microelectrode may be associated with each ablation electrode. At least some of the microelectrodes may be configured to sense tissue contact. Alternatively or in addition, at least some of the microelectrodes may be configured to sense temperature. Further, at least some of the microelectrodes may be positioned within a perimeter of at least one of the ablation electrodes.

In one aspect, each ablation electrode may have a plurality of apertures configured to perfuse irrigation fluid.

This disclosure is also directed to a catheter with an elongated catheter body having proximal and distal ends and an electrode assembly, wherein the electrode assembly is disposed over a distal portion of the catheter body and wherein the electrode assembly has a flexible substrate with a plurality of independently controlled ablation electrodes distributed radially around the electrode assembly. In one aspect, a plurality of electrode assemblies may be distributed longitudinally along the catheter body. Each electrode assembly may have two ablation electrodes positioned in opposition to each other.

This disclosure also includes a method for constructing an electrode assembly to be disposed over a catheter body. The method may include providing a flexible substrate having opposing edges, applying a plurality of independently controlled ablation electrodes to a surface of the flexible substrate, and joining the opposing edges of the substrate to form a cylinder, wherein the ablation electrodes are distributed radially around the cylinder.

In one aspect, the electrode assembly comprises two ablation electrodes positioned in opposition to each other. The method may also include applying at least one microelectrode associated with each ablation electrode to the surface of the substrate. Further, a plurality of apertures configured to perfuse irrigation fluid may be formed in the substrate and the applied ablation electrodes.

This disclosure further includes a method for the ablation of a portion of tissue of a patient by an operator. The method may involve inserting a catheter into the patient, wherein the catheter has an elongated body and an electrode assembly disposed over a distal portion of the elongated body, wherein the electrode assembly comprises a plurality of independently controlled ablation electrodes distributed radially around the electrode assembly. The catheter may be connected to a system controller capable of selectively delivering power at least one of the ablation electrodes and power to the at least one ablation electrode may be controlled to ablate tissue.

In one aspect, controlling the power to the at least one ablation electrode may cause the electrode assembly to preferentially emit energy in a radial direction.

In one aspect, signals may be received from a plurality of microelectrodes of the electrode assembly, wherein at least one microelectrode is associated with each ablation electrode and is configured to sense tissue. The power may be controlled to the at least one ablation electrode is based at least in part on the received signals.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
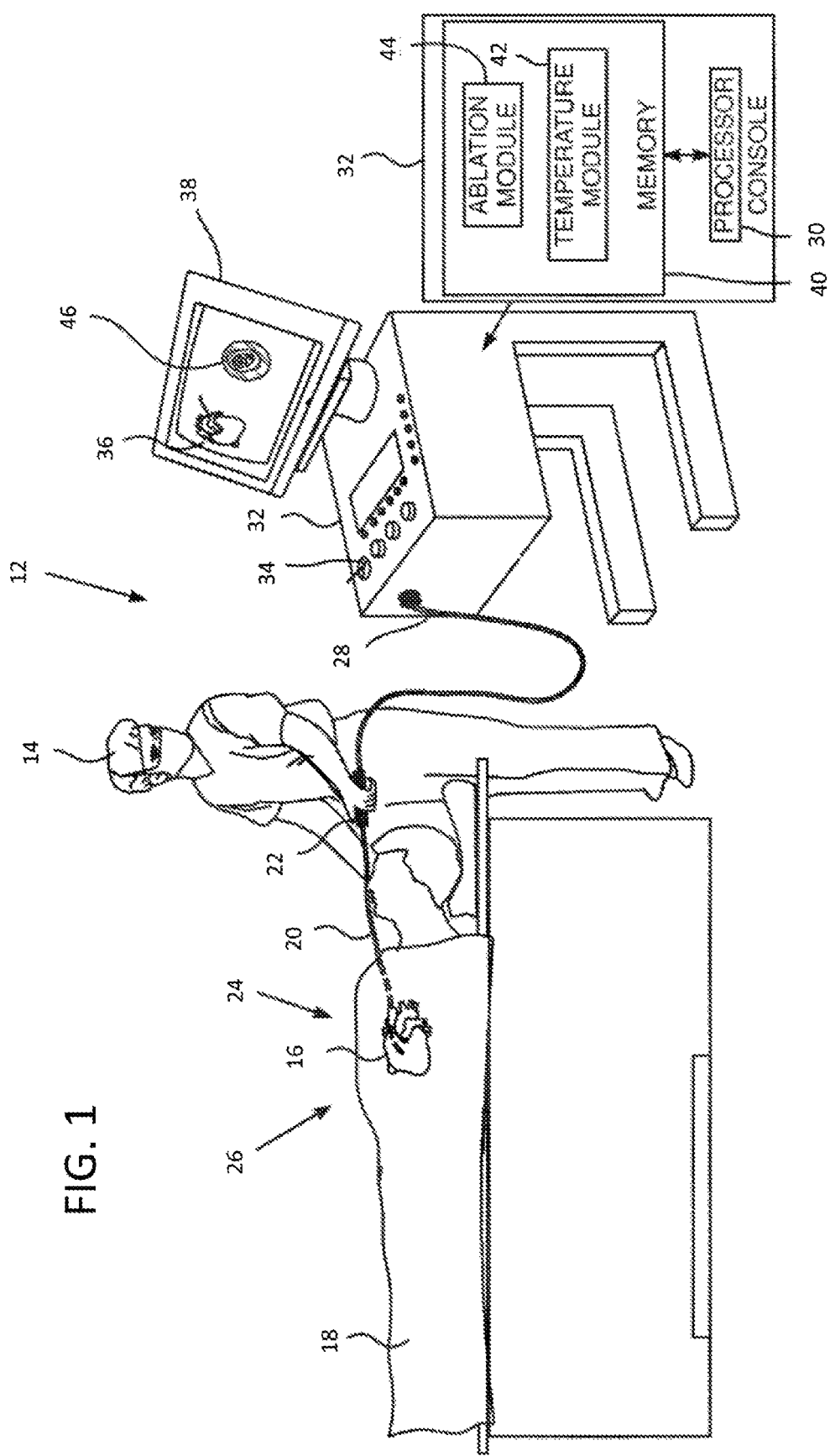
FIG. 1 is a schematic view of an ablation system in accordance with an embodiment of the present invention.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a", "an" and "the" include plural referents unless the content clearly dictates otherwise.

As noted above, certain types of electrical activity within the heart chamber may not be cyclical. For example, ventricular tachycardia originating in scars in the wall of the ventricle may be a result of infarcts. Such electrical activity is random from beat to beat. RF energy may be delivered to selected treatment areas of the epicardial tissue for ablation based therapies, including for example, isolation of a source of irregular electrical signals by blocking electrical conduction. Correspondingly, one or more electrode assemblies, each with a plurality of electrodes, may be used to deliver ablation energy in a radially selective manner. Further, each electrode assembly may have microelectrodes for tissue sensing, measurement of temperature during the ablation temperature, as well as other suitable purposes.

FIG. 1 is a schematic illustration of an invasive medical procedure using system 12, according to an embodiment of the present invention. The procedure is performed by a medical professional, operator 14, and, by way of example, the procedure in the description hereinbelow is assumed to comprise ablation of a portion of a tissue 16 of the heart of a human patient 18, such as at an area of the epicardial surface from within the pericardial cavity as discussed above. However, it will be understood that embodiments of the present invention are not applicable to this specific procedure alone and may include substantially any procedure on biological tissue or on non-biological material.

In order to perform the ablation, operator 14 inserts a catheter 20 into a lumen of the patient, using handle 22, so that a distal end 24 of the catheter enters the heart of the patient. Distal end 24 comprises at least an electrode assembly 26 for delivering ablation energy to intended locations of the heart in a radially controlled manner Catheter 20 has a proximal end 28 for connection to associated equipment as described below. Distal end 24 and in particular, electrode assembly 26, of the catheter is described in more detail with reference to FIGS. 3, 4 and 5.

System 12 is controlled by a system processor 30, which is located in an operating console 32 of the system. Console 32 comprises controls 34 which are used by professional 14 to communicate with the processor. During the procedure, processor 30 typically tracks a location and an orientation of distal end 24 of the catheter, using any method known in the art. For example, processor 30 may use a magnetic tracking method, wherein magnetic transmitters external to patient 18 generate signals in coils positioned in the distal end. The CARTO® system referenced above uses such a tracking method and additional details may be found in U.S. Pat. Nos. 5,391,199, 6,690,963, 6,484,118, 6,239,724, 6,618,612, 6,332,089, 6,690,963, 7,729,742, in PCT Patent Publication WO 96/05768, and in U.S. Patent Publication No. 2004/0068178 A1, whose disclosures are all incorporated herein by reference.

The software for processor 30 may be downloaded to the processor in electronic form, over a network, for example. Alternatively or additionally, the software may be provided on non-transitory tangible media, such as optical, magnetic, or electronic storage media. The track of distal end 24 is typically displayed on a three-dimensional representation 36 of the heart 16 of patient 18 on a screen 38. In order to operate system 12, processor 30 communicates with a memory 40, which has a number of modules used by the processor to operate the apparatus. Thus, memory 40 comprises a temperature module 42 and an ablation module 44, for example, and typically comprises other modules, such as a force module for measuring the force on end 24, a tracking module for operating the tracking method used by processor 30, and an irrigation module allowing the processor to control irrigation provided for distal end 24. For simplicity, such other modules, which may comprise hardware as well as software elements, are not illustrated in FIG. 1. Processor 30 typically uses results of measurements of temperature acquired by module 42 to display on screen 38 a temperature distribution map 46.

Figure 2:
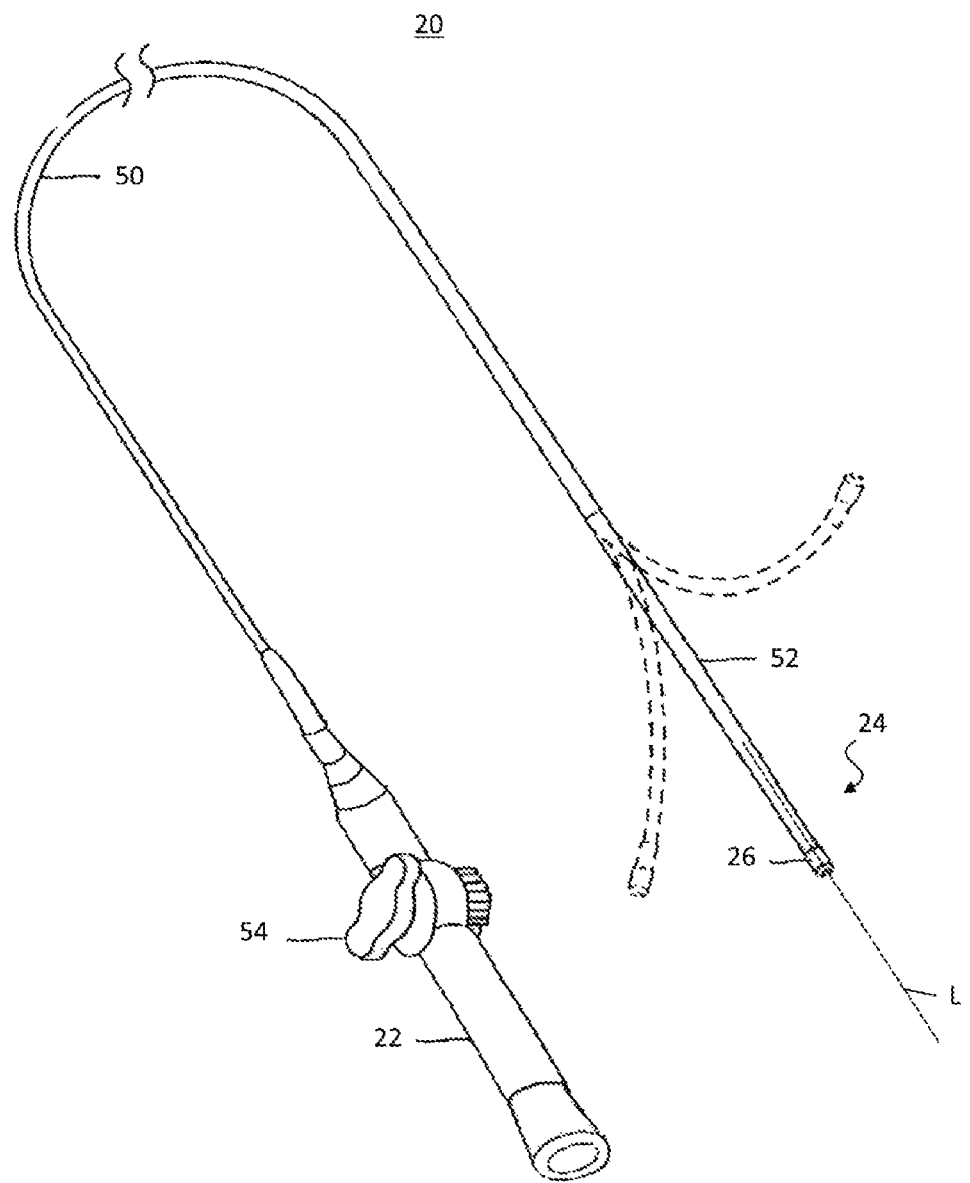
FIG. 2 is a perspective view of a catheter having selective radial energy delivery in accordance with an embodiment of the present invention.

A schematic elevational view of catheter 20 is illustrated in FIG. 2, showing an elongated body that includes an insertion shaft or catheter body 50 having a longitudinal axis "L," and an intermediate section 52 distal of the catheter body that optionally may be uni- or bi-directionally deflectable off-axis from the catheter body as indicated. Proximal of catheter body 50 is control handle 22 that allows an operator to maneuver the catheter as disclosed above, such as by deflecting intermediate section 52 when a steerable embodiment is employed. For example, control handle 22 may include deflection knob 54 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,262, 6,500,167, 6,522,933 and 8,617,087, the entire disclosures of which are incorporated herein by reference.

Catheter body 50 is flexible, i.e., bendable, but substantially non-compressible along its length and may be of any suitable construction and made of any suitable material. In one aspect, an outer wall made of polyurethane or PEBAX® (polyether block amide) may have an imbedded braided mesh of stainless steel or the like, as is generally known in the art, to increase torsional stiffness of catheter body 50 so that, when the control handle 22 is rotated, the intermediate section 52 will rotate in a corresponding manner Depending upon the intended use, the outer diameter of catheter body 50 may be approximately 8 french, and in some embodiments, may be 7 french. Likewise, the thickness of the outer wall of catheter body 50 may be thin enough so that a central lumen may accommodate any desired wires, cables and/or tubes. An example of a catheter body construction suitable for use in connection with the present invention is described and depicted in U.S. Pat. No. 6,064,905, the entire disclosure of which is incorporated herein by reference. The useful length of the catheter, i.e., that portion that can be inserted into the body may vary as desired. In exemplary embodiments, the useful length may range from about 110 cm to about 120 cm. The length of the intermediate section 52 may correspond to a relatively small portion of the useful length, such as from about 3.5 cm to about 10 cm, and in some embodiments, from about 5 cm to about 6.5 cm.

Figure 3:
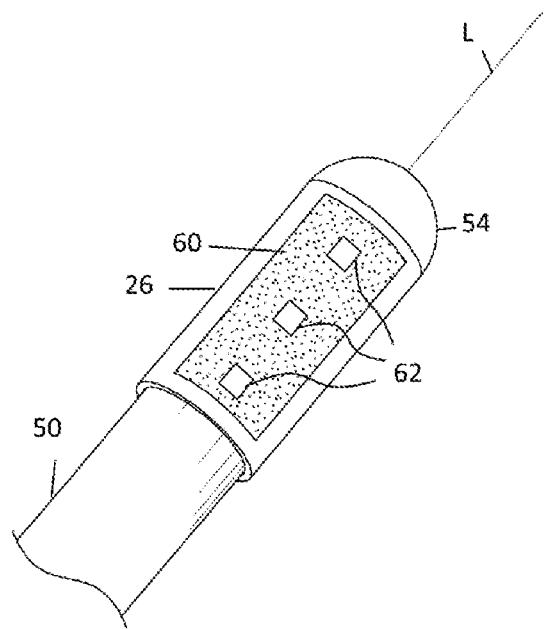
FIG. 3 is a schematic, elevational view of a distal end of the catheter of FIG. 2, showing an electrode assembly with radially distributed ablation electrodes in accordance with an embodiment of the present invention.
Figure 4:
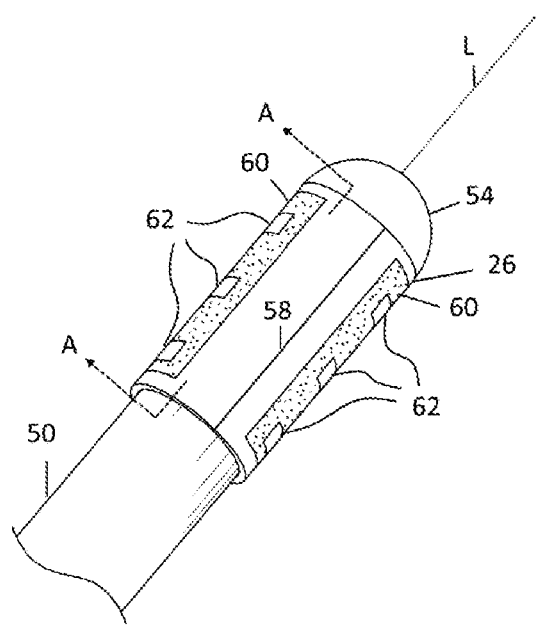
FIG. 4 is a schematic, elevational view rotated 90° from the view shown in FIG. 3.
Figure 5:
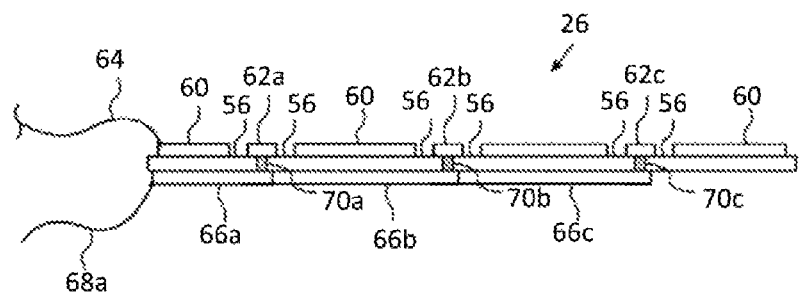
FIG. 5 is a partial, schematic cross section of an electrode assembly formed from a flexible substrate in accordance with an embodiment of the present invention.

Details regarding one embodiment of the distal end 24 of catheter 20 are illustrated in FIGS. 3, 4 and 5. As indicated, electrode assembly 26 is configured as a generally cylindrical portion that may be disposed over catheter body 50. In this embodiment, electrode assembly 26 is positioned the distal end 24 of catheter 20 which features a non-conductive, atraumatic tip 54. Electrode assembly 26 may be implemented using any suitable flexible circuit architecture, using a non-conductive substrate 56 upon which functional components and their respective leads may be printed, layered or otherwise applied as desired. For example, electrode assembly 26 may be formed from a sheet of substrate 56 by bonding opposing edges together to form a single seam 58 as shown in FIG. 4 and create a cylindrical structure to be disposed over catheter body 50.

The two elevational views shown in FIGS. 3 and 4 are rotated 90° with respect to each other about the longitudinal axis "L," to illustrate the radial distribution of two ablation electrodes 60 representative of this embodiment. As may be seen, the ablation electrodes 60 are positioned in opposition to each other on either side of electrode assembly 26, in an approximately 180° orientation. It will also be appreciated that distal end 24 may have a non-linear configuration during use, either due to directional steering control or due to a pre-shaped end. The positioning of ablation electrodes may correspondingly follow the bias of the catheter representing the deflection curve so that one of the ablation electrodes may preferentially orient towards the desired treatment area. Generally, each ablation electrode 60 may have a length in the range of 1 mm to 8 mm. In an embodiment, the length of the electrode is 3 mm With this configuration, the ablation electrode 26 most directly oriented towards the desired treatment area may be energized to form the lesion, while the other ablation electrode 60 is not used, thereby reducing exposure of surrounding areas to RF energy. In the context of an epicardial procedure similar to that described above, using only one of the two ablation electrodes 60 may allow delivery of energy towards the epicardial surface while minimizing the delivery of energy towards the pericardium, other organs, the nervous system, or other unintended areas. It should be appreciated that the techniques of this disclosure are not limited to the use of two ablation electrodes and any suitable number and radial distribution of electrodes may be employed as discussed below.

As shown, electrode assembly 26 may also comprise microelectrodes 62 positioned within the perimeter of ablation electrodes 60 as shown, or in other embodiments, at locations proximate to the ablation electrodes. Microelectrodes 62 may be configured to sense tissue contact, such as by comparing measured electrical characteristics including impedance. Feedback from microelectrodes 62 may be analyzed to determine which ablation electrode 60 should be energized to control the radial delivery of RF energy. In embodiments having more than two ablation electrodes, it may be desirable to energize more than one of the electrodes as warranted. Microelectrodes 62 may also be configured as thermocouples or other suitable temperature sensors in order to monitor conditions during ablation. Microelectrodes 62 configured as temperature sensors may typically be copper-constantan thermocouples, but other techniques may be used, and may be arrayed at locations around electrode assembly 26, both axially and circumferentially. Any suitable number of microelectrodes 62 may be configured as thermocouples in order to achieve the desired resolution of sensing. As yet another example, microelectrodes 62 may also be configured to record signals for mapping electrical activity of the heart, such as to identify treatment areas to be ablated. Microelectrodes 62 are connected by leads (not shown in these views) running through the length of catheter body 50 to provide their signals to respective components of console 32, such as temperature module 42 and ablation module 44.

Typically, distal end 24 contains other functional components, which are outside the scope of the present disclosure and are therefore omitted for the sake of simplicity. For example, the distal end of the catheter may contain steering wires, as well as sensors of other types, such as a position sensor and a force sensor. Catheters containing components of these kinds are described, for example, in U.S. Pat. No. 8,437,832 and U.S. Patent Publication No. 2011/0130648, which are incorporated herein by reference.

Reference is now additionally made to FIG. 5, which shows a cross sectional view through electrode assembly 26 at one of the ablation electrodes 60 as indicated by line "A" in FIG. 4. This figure shows additional details of the construction of electrode assembly 26 and its flexible electronic circuits. Such flex circuits or flexible electronics involve a technology for assembling electronic circuits by mounting electronic devices on flexible plastic substrates, such as polyimide, Liquid Crystal Polymer (LCP), PEEK or transparent conductive polyester film (PET). Additionally, flex circuits can be screen printed silver circuits on polyester. Flexible printed circuits (FPC) may be made with a photo-lithographic technology. An alternative way of making flexible foil circuits or flexible flat cables (FFCs) is laminating very thin (approximately 0.07 mm) copper strips in between two layers of PET. These PET layers, typically approximately 0.05 mm thick, are coated with an adhesive which is thermosetting, and will be activated during the lamination process. Single-sided flexible circuits have a single conductor layer made of either a metal or conductive (metal filled) polymer on a flexible dielectric film. Component termination features may be accessible only from one side and holes may be formed in the base film to allow component leads to pass through for interconnection, normally by soldering.

One exemplary architecture is shown in FIG. 5, but any suitable implementation may be employed. Substrate 56 may have a first conducting layer from which ablation electrode 60 and microelectrodes 62a, 62b and 62c are formed. The electrode layer may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium), or the like. Lead 64 connects the ablating electrode 60 and runs through catheter body 50 to couple with console 32, for delivery of RF energy supplied by ablation module 44. A second conducting layer on the other side of substrate 56 may be used to provide connection to microsensors 62a, 62b and 62c via respective traces 66a, 66b and 66c. For clarity, only lead 68a is shown, but each trace may be connected to a lead to transmit signals through catheter body 50. Each respective trace may be connected to its associated microelectrode through plated holes 70a, 70b and 70c (sometimes referred to as "vias") or other electrically-conductive interconnection through substrate 56. Thus, depicted lead 64 and a corresponding lead that is also not shown for clarity may convey RF electrical energy from ablation module 44 of console 32, which may control the level of power dissipated, to electrode assembly 26 through catheter body 50. Similarly, microelectrodes 62 are connected by leads 68 running through the length of catheter body 50 to provide their signals to respective components of console 32, such as temperature module 42 and ablation module 44. Correspondingly, either ablation electrode 60 may be selectively energized to ablate myocardial tissue, depending on which electrode is chosen. As discussed above, this may involve using the signals from microelectrodes 62 to determine which ablation electrode 60 is oriented more desirably with respect to the intended treatment area. Once again, in embodiments having more than two ablation electrodes, control over the radial delivery of energy may involve energizing a single electrode or a subset of adjacent electrodes. Still further, any desired pattern of electrode activation may be employed in other applications. Module 44 may control the level of RF power dissipated via electrode assembly 26.

Figure 6:
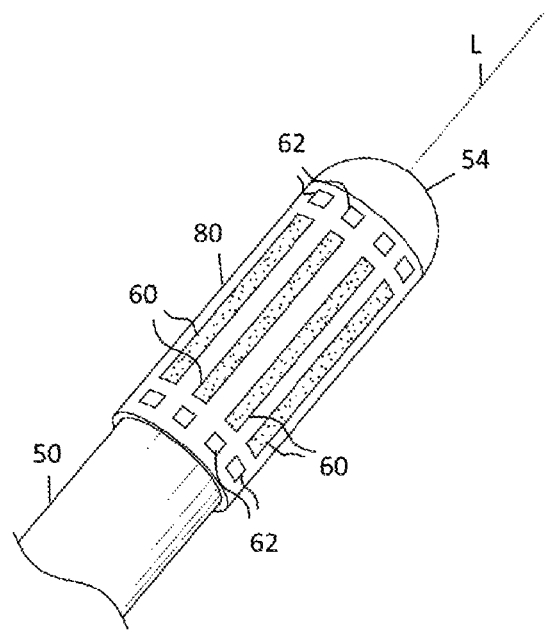
FIG. 6 is a schematic, elevational view of a distal end of a catheter having an alternative electrode assembly with radially distributed ablation electrodes in accordance with an embodiment of the present invention.

As noted above, the techniques of this disclosure may be extended to employ any desired number of ablation electrodes. For example, an alternative embodiment is shown in FIG. 6, with electrode assembly 80 similarly disposed over catheter body 50. In the depicted embodiment, electrode assembly 80 features 10 individually controlled ablation electrodes 60 (although only four are visible in this view). Further, this embodiment features a pair of microelectrodes 62 for each ablation electrode that are positioned proximally and distally, rather than being within the perimeter of the ablation electrode. Regardless of the exact location of the microelectrodes, it will be appreciated that by associating at least one microelectrode with each ablation electrode, the conditions and characteristics of that ablation electrode may be determined. In other embodiments, any suitable number of ablation electrodes may be employed with any desired radial distribution. For example, four ablation electrodes may be used to provide coverage of quadrants around the circumference of catheter body 50. Equally, any number of microelectrodes may also be used, depending on the desired sensing resolution or other suitable criteria. Similarly, although the embodiments depicted in this disclosure have generally even radial distribution, other distributions may be employed to concentrate a greater number of ablation electrodes in one or more radial areas. Likewise, even though the depicted ablation electrodes have generally the same size and configuration, the ablation electrodes may vary in either size or configuration in other embodiments as desired.

Figure 7:
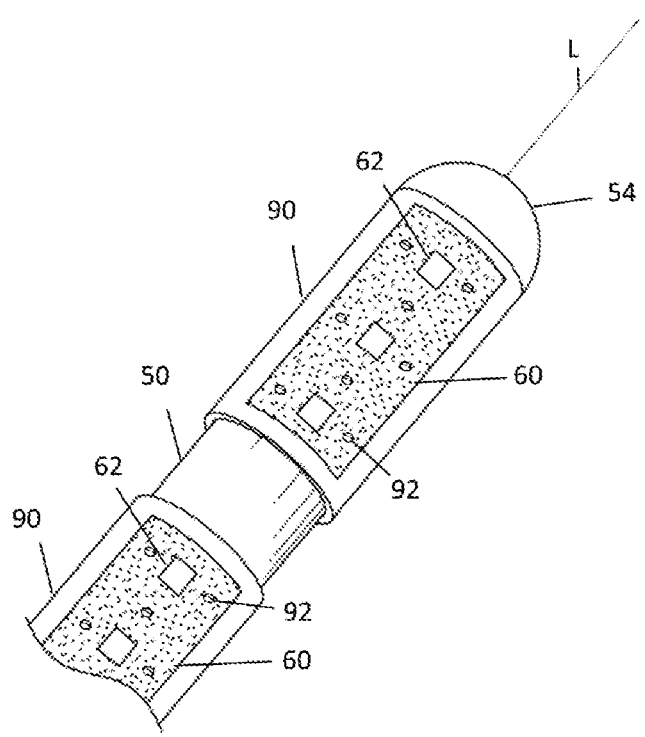
FIG. 7 is a schematic, elevational view of a distal end of a catheter having an multiple electrode assemblies distributed longitudinally along the catheter body in accordance with an embodiment of the present invention.

In another aspect, multiple electrode assemblies may be employed as well. For example, FIG. 7 schematically depicts an embodiment in which at least two electrode assemblies 90 are positioned relatively proximally and distally along the length of catheter body 50, although still generally towards distal end 24. As shown, each electrode assembly 90 may have two ablation electrodes 60, oriented approximately 180° with respect to each other in a manner similar to electrode assembly 26. Likewise, each ablation electrode has three microelectrodes 62 in this embodiment, but again, any suitable number may be used as desired. Any number of electrode assemblies 90 may be distributed longitudinally along catheter body 50.

Another aspect of this disclosure as depicted in FIG. 7 involves providing electrode assemblies 90 with a plurality of apertures 92 for the perfusion of irrigation fluid, delivered via a lumen (not shown) in catheter 20. Cooling fluid may exit through apertures 92 to help control temperature of the tissue during ablation. When the electrode reaches critical temperatures, denaturation of blood proteins causes coagulum formation. Impedance can then rise and limit current delivery. Moreover, overheating within tissue can cause steam bubble formation (steam "pops") with risk of uncontrolled tissue destruction or undesirable perforation of bodily structures. Thus, the ablation catheters of this disclosure may be irrigated to provide greater control over the temperature of catheter components and the surrounding tissue. As an example of similar techniques, Biosense Webster Inc. (Diamond Bar, Calif.) offers the ThermoCool® irrigated-tip catheter for use with its CARTO® integrated mapping and ablation system. A pump coupled to the catheter delivers saline solution or other suitable fluid through the catheter lumen to distal end 24 so that it may flow through apertures 92 during the procedure in order to cool the catheter tip and the tissue. In addition to saline, other fluids such as heparin, can be transported to the ablation site to cool tissue, reduce coagulation and/or facilitate the formation of deeper lesions. It is understood that other fluids can be delivered, as well, including any diagnostic and therapeutic fluids, such as neuroinhibitors and neuroexcitors for altering the state of ganglionated plexi. Representative details concerning irrigated ablation catheters may be found in commonly-owned U.S. Pat. No. 9,675,411, whose disclosure is incorporated herein by reference in its entirety.

Likewise, it may also be desirable to accurately monitor temperature to help control the rate of irrigation. Notably, microelectrodes 62, configured as temperature sensors, may be positioned at different locations to measure temperature at the corresponding outer surfaces of electrode assembly 90. As discussed above, such microelectrodes may be within the perimeter of the ablation electrodes or otherwise in proximity, but generally are positioned on the surface of electrode assembly 90 and may be spaced apart from apertures 92. Microelectrodes 62 may thus provide multiple temperature readings that are substantially independent of the cooling fluid temperature, at different locations on electrode assembly 90. The sensor that gives the highest temperature reading may be the one that is in contact with the tissue being ablated, and the temperature measured by this sensor varies linearly with the actual tissue temperature. Flow of the irrigation fluid may be generally lower in areas that are in firm contact with the tissue, and the sensors in these areas typically give the highest temperature readings. In some applications, the reading from the "hottest" sensor may thus be used in particular to monitor the tissue temperature and control the applied power and duration of the ablation procedure in order to obtain the desired therapeutic result without excessive tissue damage. Alternatively or additionally, the temperature readings of the multiple sensors can be combined and interpolated to give a map of temperature over the area of the catheter tip.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrode assembly configured to be disposed longitudinally over a distal portion of a cylindrical catheter body proximal to a tip of the catheter body, the electrode assembly comprising:
a flexible substrate forming a cylinder over the distal portion of the cylindrical catheter body proximal the tip, the cylindrical flexible substrate having: i) a first independently controlled ablation electrode formed by a first longitudinal electrically conducting layer applied directly to the outer surface of the cylindrical flexible substrate, ii) a second independently controlled ablation electrode formed by a second longitudinal electrically conducting layer applied directly to the outer surface of the cylindrical flexible substrate, iii) a first plurality of associated microelectrodes formed within a perimeter of the first ablation electrode, wherein an empty space is disposed between the first ablation electrode and at least one microelectrode of the first plurality of microelectrodes, and iv) a second plurality of associated microelectrodes formed within a perimeter of the second ablation electrode, wherein the first and second ablation electrodes and their associated microelectrodes, respectively, are positioned diametrically opposed to each other circumferentially on the cylindrical flexible substrate.

2. The electrode assembly of claim 1, comprising more than two ablation electrodes.

3. The electrode assembly of claim 1, wherein at least some of the microelectrodes are configured to sense tissue contact.

4. The electrode assembly of claim 1, wherein at least some of the microelectrodes are temperature sensors.

5. The electrode assembly of claim 1, wherein each ablation electrode has a plurality of apertures configured to perfuse irrigation fluid.

6. A method for the ablation of a portion of tissue of a patient by an operator comprising:
inserting a catheter into the patient, wherein the catheter comprises:
an elongated cylindrical body having a distal portion proximal to a tip; and
an electrode assembly disposed longitudinally over the distal portion of the cylindrical elongated body proximal the tip, wherein the electrode assembly comprises a flexible substrate forming a cylinder over the distal portion of the cylindrical catheter body proximal the tip, the cylindrical flexible substrate having: i) a first independently controlled ablation electrode formed by a first longitudinal electrically conducting layer applied directly to the outer surface of the cylindrical flexible substrate, ii) a second independently controlled ablation electrode formed by a second longitudinal electrically conducting layer applied directly to the outer surface of the cylindrical flexible substrate, iii) a first plurality of associated microelectrodes formed within a perimeter of the first ablation electrode, wherein an empty space is disposed between the first ablation electrode and at least one microelectrode of the first plurality of microelectrodes, and iv) a second plurality of associated microelectrodes formed within a perimeter of the second ablation electrode, wherein the first and second ablation electrodes and their associated microelectrodes, respectively, are positioned diametrically opposed to each other circumferentially on the cylindrical flexible substrate;

connecting the catheter to a system controller capable of selectively delivering power to at least one of the ablation electrodes; and controlling the power to at least one of the ablation electrodes to ablate the portion of the tissue.

7. The method of claim 6, wherein controlling the power to at least one of the ablation electrodes causes the electrode assembly to preferentially emit energy in a radial direction.

8. The method of claim 6, further comprising receiving signals from a plurality of microelectrodes of the electrode assembly, wherein at least some of the microelectrodes are configured to sense tissue and wherein controlling the power to at least one of the ablation electrodes is based at least in part on the received signals.

* * * * *